United States Patent
Lee et al.

(10) Patent No.: US 9,328,056 B2
(45) Date of Patent: May 3, 2016

(54) METHOD FOR PREPARING CARBONIC ESTER USING ORGANOMETALLIC COMPOUND

(71) Applicant: Samsung SDI Co., Ltd., Yongin-si (KR)

(72) Inventors: Yeon Ju Lee, Uiwang-si (KR); Dong Baek Kim, Uiwang-si (KR); Jong Won Lee, Uiwang-si (KR); Chang Hoon Lee, Uiwang-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 0 days.

(21) Appl. No.: 14/697,757

(22) Filed: Apr. 28, 2015

(65) Prior Publication Data

US 2015/0315121 A1    Nov. 5, 2015

(30) Foreign Application Priority Data

Apr. 30, 2014  (KR) .................. 10-2014-0052797

(51) Int. Cl.
*C07C 68/04* (2006.01)

(52) U.S. Cl.
CPC ..................... *C07C 68/04* (2013.01)

(58) Field of Classification Search
None
See application file for complete search history.

(56) References Cited

U.S. PATENT DOCUMENTS

| 7,313,128 | B2 | 12/2007 | Andersen et al. | |
|---|---|---|---|---|
| 7,435,842 | B2* | 10/2008 | Miyake et al. | 558/260 |
| 2008/0177099 | A1 | 7/2008 | Miyake | |
| 2010/0043672 | A1 | 2/2010 | Jesse et al. | |

FOREIGN PATENT DOCUMENTS

| JP | 2005-511122 A | 4/2005 |
|---|---|---|
| JP | 2006-513613 A | 4/2006 |
| JP | 2007-269653 A | 10/2007 |
| JP | 4159097 A | 7/2008 |
| JP | 4218976 B2 | 2/2009 |
| JP | 2010-523783 A | 7/2010 |
| WO | 03/030790 A1 | 4/2003 |

* cited by examiner

*Primary Examiner* — Michael Barker
*Assistant Examiner* — Po-Chih Chen
(74) *Attorney, Agent, or Firm* — Additon, Higgins & Pendleton, P.A.

(57) ABSTRACT

A method for preparing a carbonic ester includes reacting carbon dioxide and a $C_1$ to $C_{10}$ alcohol with an organometallic compound represented by Formula 1. With the method, carbonic ester can be prepared in high yield without recycling the organometallic compound.

$$M(OR^1)_4 \quad \text{[Formula 1]}$$

wherein M is a Group IV or Group XIV element and each $R^1$ is independently a $C_1$ to $C_{10}$ hydrocarbon group.

5 Claims, No Drawings

METHOD FOR PREPARING CARBONIC ESTER USING ORGANOMETALLIC COMPOUND

CROSS-REFERENCE TO RELATED APPLICATION

This application claims priority under 35 USC Section 119 to and the benefit of Korean Patent Application 10-2014-0052797, filed on Apr. 30, 2014, the entire disclosure of which is incorporated herein by reference.

FIELD OF THE INVENTION

The present invention relates to a method for preparing a carbonic ester using an organometallic compound.

BACKGROUND

A carbonic ester is a monomer useful in preparation of polycarbonates, and many studies have been made on preparation of the carbonic ester. Conventionally, a carbonic ester has been prepared through reaction of an alcohol with phosgene as a carbonyl source. However, this method has a problem of use of phosgene, which is a very toxic compound, and also brings problems with use of a chlorinated solvent and disposal of neutral by-product salts.

To overcome these problems, a method for preparing a carbonic ester using carbon monoxide as a carbonyl source has been developed. However, when carbon monoxide is used as a carbonyl source, there are problems of reduction in reaction speed and yield, a high risk of explosion due to use of toxic carbon monoxide at high pressure, and costs for securing safety. In addition, there is a concern of side reactions, such as generation of carbon dioxide caused by oxidation of carbon monoxide.

There has also been developed a method wherein carbon dioxide is reacted with ethylene oxide and the like to prepare a cyclic carbonic ester, followed by reacting the cyclic carbonic ester with methanol, producing dimethyl carbonate. This method has advantages in that harmless carbon dioxide is used as a carbonyl source, and corrosive materials are hardly generated. However, this method can cause side reactions such as generation of ethylene glycol, and has a limitation relating to plant location due to difficulty in safe transport of ethylene oxide or ethylene, which is a source of ethylene oxide.

Recently, a method for preparing a carbonic ester by reacting carbon dioxide with an organometallic compound has been studied. It has also been found that, after separation of a carbonic ester from a mixture produced by the method, the organometallic compound can be reproduced by reaction of a residual liquid with an alcohol. In other words, the used organometallic compound can be recycled to be reused in formation of the carbonic ester, thereby eliminating transport-related problems. As such an organometallic compound, there are disclosed compounds in the form of $Sn(R)_2(OR')_2$ (R and R' being two different alkyl groups) which includes tin as a center metal and contains two alkyl groups and an alkoxy group (Japanese Patent Publication No. 2010-523783 A, No. 2006-548937 A, No. 2006-513613 A, No. 2007-269653 A, No. 2005-511122 A, No. 2003-556375 A, and the like). However, these known organometallic compounds have a problem of low reactivity and reduction in production yield of a carbonic ester. Therefore, there is a need for a method which can overcome these problems.

SUMMARY

Embodiments of the present invention provide a method for preparing a carbonic ester using an organometallic compound, in which a carbonic ester can be prepared in high yield using a specific organometallic compound, carbon dioxide, and an alcohol and/or without requiring a process of recycling the organometallic compound.

The method includes preparing a carbonic ester by reacting carbon dioxide and a $C_1$ to $C_{10}$ alcohol with an organometallic compound represented by Formula 1:

$$M(OR^1)_4 \quad \text{[Formula 1]}$$

wherein M is a Group IV or Group XIV element and each $R^1$ is independently a $C_1$ to $C_{10}$ hydrocarbon group.

In exemplary embodiments, M may be titanium (Ti) or zirconium (Zr).

In exemplary embodiments, each $R^1$ may independently be a methyl group, an ethyl group, an n-propyl group, an isopropyl group, an n-butyl group, an isobutyl group, a tert-butyl group, an n-pentyl group, an isopentyl group, an n-hexyl group, and/or a phenyl group.

In exemplary embodiments, the reaction may be performed at a temperature of about 130° C. to about 230° C. and at a carbon dioxide pressure of about 10 bar to about 300 bar.

In exemplary embodiments, the organometallic compound may be reused without a process of recycling the organometallic compound.

DETAILED DESCRIPTION

Exemplary embodiments now will be described more fully hereinafter in the following detailed description, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

A method for preparing a carbonic ester according to the invention includes preparing a carbonic ester by reacting an organometallic compound with carbon dioxide and a $C_1$ to $C_{10}$ alcohol at the same time.

The organometallic compound used in the present invention may be represented by Formula 1.

$$M(OR^1)_4 \quad \text{[Formula 1]}$$

wherein M may be a Group IV or Group XIV element, for example, titanium (Ti), tin (Sn), or zirconium (Zr), for example titanium or zirconium, and each $R^1$ may independently be a $C_1$ to $C_{10}$ hydrocarbon group, for example, a $C_1$ to $C_8$ alkyl group and/or a $C_6$ to $C_{10}$ aryl group, and as another example a methyl group, a ethyl group, an n-propyl group, an isopropyl group, an n-butyl group, an isobutyl group, a tert-butyl group, an n-pentyl group, an isopentyl group, an n-hexyl group, and/or a phenyl group.

Examples of the organometallic compound may include without limitation tetramethoxy zirconium, tetramethoxy titanium, tetraethoxy zirconium, tetraethoxy titanium, tetra-n-propoxy zirconium, tetra-n-propoxy titanium, tetraisopropoxy zirconium, tetraisopropoxy titanium, tetra-n-butoxy zirconium, tetra-n-butoxy titanium, tetra-isobutoxy zirconium, tetraisobutoxy titanium, tetra-tert-butoxy zirconium, tetra-tert-butoxy titanium, tetra-n-pentoxy zirconium, tetra-n-pentoxy titanium, tetra-3-methyl-1-butoxy zirconium, tetra-3-methyl-1-butoxytitanium, tetra-n-hexanoxy zirconium, tetra-n-hexanoxy titanium, tetra-n-phenoxy zirconium, tetra-n- phenoxy titanium, and the like, and combinations thereof. In exemplary embodiments, the organometallic compound may include tetra-n-propoxy titanium, tetra-n-butoxy zirconium, tetra-n-butoxy titanium, and/or tetra-3-methyl-1-butoxy titanium, and the like.

The alcohol used in the present invention may be represented by Formula 2.

$$R^2OH \qquad \text{[Formula 2]}$$

wherein $R^2$ may be a $C_1$ to $C_{10}$ hydrocarbon group, for example, a $C_1$ to $C_8$ alkyl group or a $C_6$ to $C_{10}$ aryl group, and as another example a methyl group, an ethyl group, an n-propyl group, an isopropyl group, an n-butyl group, an isobutyl group, a tert-butyl group, an n-pentyl group, an isopentyl group, an n-hexyl group, or a phenyl group. In exemplary embodiments, $R^1$ and $R^2$ may be the same hydrocarbon group.

Examples of the alcohol may include without limitation methanol, ethanol, n-propanol, isopropanol, n-butanol, isobutanol, tert-butanol, n-pentanol, isopentanol, n-hexanol, phenol, and the like, and combinations thereof.

A carbonic ester prepared by the method for preparing a carbonic ester according to the invention may be represented by Formula 3.

$$R^3OCOOR^4 \qquad \text{[Formula 3]}$$

wherein $R^3$ and $R^4$ are the same or different and may each independently be a $C_1$ to $C_{10}$ hydrocarbon group, for example, a $C_1$ to $C_8$ alkyl group and/or a $C_6$ to $C_{10}$ aryl group, and as another example a methyl group, an ethyl group, an n-propyl group, an isopropyl group, an n-butyl group, an isobutyl group, a tert-butyl group, an n-pentyl group, an isopentyl group, an n-hexyl group, and/or a phenyl group. $R^3$ and $R^4$ may be derived from $R^1$ of the organometallic compound and $R^2$ of the alcohol.

In exemplary embodiments, the method for preparing a carbonic ester may be carried out by a batch reaction, a continuous reaction, and the like.

In the method for preparing a carbonic ester according to exemplary embodiments of the invention, the reaction may be performed by typical batch reaction. For example, reaction may be performed at a temperature of about 130° C. to about 230° C., for example, at about 140° C. to about 190° C., and at a carbon dioxide pressure of about 10 bar to about 300 bar, for example, about 40 bar to about 290 bar. Within this range, it is possible to secure rapid reaction and to prepare a carbonic ester in high yield. Typically, batch reaction is performed in consideration of a conversion rate and a volume of a reactor, and is a solution process avoiding overheating.

In addition, the reaction is performed using a $C_1$ to $C_{10}$ alcohol, which is a liquid reactant, carbon dioxide which is a gaseous reactant, and a solid organometallic compound, and thus does not require a separate solvent. In other words, the reaction may be homogeneous reaction wherein carbon dioxide and the organometallic compound are dissolved in the alcohol to react with one another. Mixing in a reactor may be performed using a magnetic bar, a mechanical mixer, and the like, and may be performed at a mixing speed of about 300 rpm to about 1,000 rpm, for example, about 400 rpm to about 500 rpm for a reaction time of about 0.5 hours to about 24 hours, for example, about 1 hour to about 3 hours. The reaction can be performed in a region where mass transfer at an interface between carbon dioxide and the alcohol has a maximum value in view of a state of the organometallic compound and viscosity of a solvent. Such batch reaction can be easily performed by those skilled in the art.

For example, in this method, the carbonic ester can be produced by reaction represented by Reaction Formula 1.

[Formula 1]

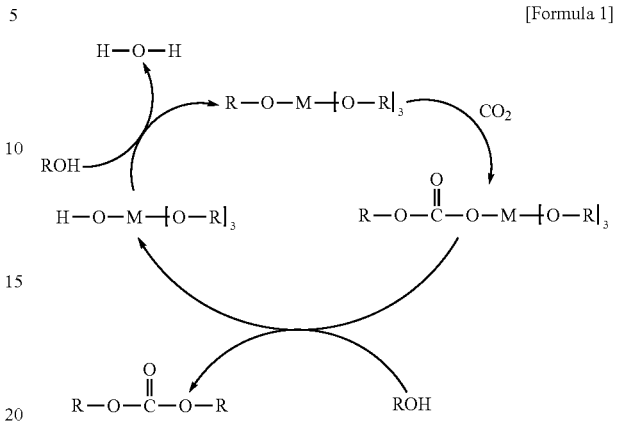

wherein each R may be the same or different and may be a $C_1$ to $C_{10}$ hydrocarbon group, for example, a $C_1$ to $C_8$ alkyl group and/or a $C_6$ to $C_{10}$ aryl group, and as another example a methyl group, an ethyl group, an n-propyl group, an isopropyl group, an n-butyl group, an isobutyl group, a tert-butyl group, an n-pentyl group, an isopentyl group, an n-hexyl group, and/or a phenyl group.

In exemplary embodiments, the organometallic compound may be added in an amount of about 1 part by mole to about 100 parts by mole, for example, about 3 parts by mole to about 60 parts by mole, based on about 100 parts by mole of the alcohol. Within this range, the carbonic ester can be produced in high yield.

In the method for preparing a carbonic ester according to the invention, the organometallic compound is reacted with carbon dioxide and the $C_1$ to $C_{10}$ alcohol at the same time, whereby the carbonic ester can be obtained in high yield.

In addition, in the method for preparing a carbonic ester, the organometallic compound can be reused without a process of recycling the organometallic compound. Specifically, the organometallic compound may be contained in a residual liquid after separation of the carbonic ester, the $C_1$ to $C_{10}$ alcohol, and impurities such as water from a product obtained by the method for preparing a carbonic ester.

Hereinafter, the present invention will be described in more detail with reference to the following examples. However, it should be understood that these examples are provided for illustration only and are not to be construed in any way as limiting the present invention.

EXAMPLE

Example 1

Preparation of Carbonic Ester

In a 40 ml autoclave reactor with an external heater, 6.25 g (tetra-n-butoxy zirconium: 13 mmol, n-butanol: 16.9 mmol) of a tetra-n-butoxy zirconium ($Zr[O(CH_2)_3CH_3]_4$) solution (80% by weight, solvent: n-butanol) and 22.9 g (309 mmol) of n-butanol are placed, followed by replacing oxygen in the reactor with carbon dioxide. Next, the reactor is heated to 180° C. while stirring, and carbon dioxide is introduced to a pressure of 120 bar, followed by reaction at 180° C. at 120 bar for 1 hour and cooling to room temperature. Thereafter, carbon dioxide is discharged to return the reactor to atmospheric pressure, followed by analyzing a reaction product through gas chromatography. It is confirmed that di-n-butyl carbonate is obtained in a yield of 169%.

Example 2

Preparation of Carbonic Ester

Reaction is performed in the same manner as in Example 1 except that reaction pressure (carbon dioxide pressure) is set to 60 bar. After completion of reaction, a reaction product is analyzed through gas chromatography. It is confirmed that di-n-butyl carbonate is obtained in a yield of 110%.

Example 3

Preparation of Carbonic Ester

In a 40 ml autoclave reactor with an external heater, 3.17 g (8 mmol) of tetra-3-methyl-1-butoxy titanium ($Ti[O(CH_2)_2CH(CH_3)_2]_4$) and 17.63 g (200 mmol) of 3-methyl-1-butanol are placed, followed by replacing oxygen in the reactor with carbon dioxide. Next, the reactor is heated to 180° C. while stirring, and carbon dioxide is introduced to a pressure of 280 bar, followed by reaction at 180° C. at 280 bar for 1 hour and cooling to room temperature. Thereafter, carbon dioxide is discharged to return the reactor to atmospheric pressure, followed by analyzing a reaction product through gas chromatography. It is confirmed that di-3-methyl-1-butyl carbonate is obtained in a yield of 74%.

Example 4

Preparation of Carbonic Ester

Reaction is performed in the same manner as in Example 3 except that 19.81 g (50 mmol) of tetra-3-methyl-1-butoxy titanium ($Ti[O(CH_2)_2CH(CH_3)_2]_4$) and 8.82 g (100 mmol) of 3-methyl-1-butanol are used, and reaction pressure (carbon dioxide pressure) is set to 260 bar. After completion of reaction, a reaction product is analyzed through gas chromatography. It is confirmed that di-3-methyl-1-butyl carbonate is obtained in a yield of 73%.

Example 5

Preparation of Carbonic Ester

In a 40 ml autoclave reactor with an external heater, 5 g (14.7 mmol) of tetra-n-butoxy titanium ($Ti[O(CH_2)_3(CH_3)]_4$) and 27.2 g (367.3 mmol) of n-butanol are placed, followed by replacing oxygen in the reactor with carbon dioxide. Next, the reactor is heated to 180° C. while stirring, and carbon dioxide is introduced to a pressure of 120 bar, followed by reaction at 180° C. at 120 bar for 1 hour and cooling to room temperature. Thereafter, carbon dioxide is discharged to return the reactor to atmospheric pressure, followed by analyzing a reaction product through gas chromatography. It is confirmed that di-n-butyl carbonate is obtained in a yield of 98%.

Example 6

Preparation of Carbonic Ester

Reaction is performed in the same manner as in Example 5 except that reaction pressure (carbon dioxide pressure) is set to 60 bar. After completion of reaction, a reaction product is analyzed through gas chromatography. It is confirmed that di-n-butyl carbonate is obtained in a yield of 82%.

Example 7

Preparation of Carbonic Ester

In a 40 ml autoclave reactor with an external heater, 5 g (17.6 mmol) of tetra-n-propoxy titanium ($Ti[O(CH_2)_2(CH_3)]_4$) and 26.4 g (439.8 mmol) of n-propanol are placed, followed by replacing oxygen in the reactor with carbon dioxide. Next, the reactor is heated to 180° C. while stirring, and carbon dioxide is introduced to a pressure of 120 bar, followed by reaction at 180° C. at 120 bar for 1 hour and cooling to room temperature. Thereafter, carbon dioxide is discharged to return the reactor to atmospheric pressure, followed by analyzing a reaction product through gas chromatography. It is confirmed that di-n-propyl carbonate is obtained in a yield of 70%.

Example 8

Preparation of Carbonic Ester

Reaction is performed in the same manner as in Example 7 except that reaction pressure (carbon dioxide pressure) is set to 60 bar. After completion of reaction, a reaction product is analyzed through gas chromatography. It is confirmed that di-n-butyl carbonate is obtained in a yield of 65%.

Example 9

Preparation of Carbonic Ester

A solution containing di-n-butyl carbonate obtained in Example 5 is placed in a 100 mL flask, followed by vacuum distillation at 90° C. to 100° C. at 20 torr, thereby separately obtaining a mixed distillate of di-n-butyl carbonate, n-butanol, and water, and a distilled residue of the titanium catalyst (tetra-n-butoxy titanium ($Ti[O(CH_2)_3(CH_3)]_4$)). Reaction in Example 5 is performed again using the distilled residue (tetra-n-butoxy titanium 5 g (14.7 mmol)). After completion of reaction, a reaction product is analyzed through gas chromatography. It is confirmed that di-n-butyl carbonate is obtained in a yield of 97%.

Comparative Example 1

Preparation of Carbonic Ester

In a 40 ml autoclave reactor with an external heater, 10 g (26 mmol) of tetra-n-butoxy zirconium ($Zr[O(CH_2)_3CH_3]_4$) is placed, followed by replacing oxygen in the reactor with carbon dioxide. Next, the reactor is heated to 180° C. while stirring, and carbon dioxide is introduced to a pressure of 120 bar, followed by reaction at 180° C. at 120 bar for 1 hour and cooling to room temperature. Thereafter, carbon dioxide is discharged to return the reactor to atmospheric pressure, followed by analyzing a reaction product through gas chromatography. It is confirmed that di-n-butyl carbonate is obtained in a yield of 67%.

Comparative Example 2

Preparation of Carbonic Ester

Reaction is performed in the same manner as in Comparative Example 1 except that reaction pressure (carbon dioxide pressure) is set to 60 bar. After completion of reaction, a reaction product is analyzed through gas chromatography. It is confirmed that di-n-butyl carbonate is obtained in a yield of 55%.

Comparative Example 3

Preparation of Carbonic Ester

In a 40 ml autoclave reactor with an external heater, 19.81 g (50 mmol) of tetra-3-methyl-1-butoxy titanium (Ti[O(CH$_2$)$_2$CH(CH$_3$)$_2$]$_4$) is placed, followed by replacing oxygen in the reactor with carbon dioxide. Next, the reactor is heated to 180° C. while stirring, and carbon dioxide is introduced to a pressure of 230 bar, followed by reaction at 180° C. at 230 bar for 1 hour and cooling to room temperature. Thereafter, carbon dioxide is discharged to return the reactor to atmospheric pressure, followed by analyzing a reaction product through gas chromatography. It is confirmed that di-3-methyl-1-butyl carbonate is obtained in a yield of 63%.

Comparative Example 4

Preparation of Carbonic Ester

Reaction is performed in the same manner as in Comparative Example 3 except that reaction pressure (carbon dioxide pressure) is set to 80 bar. After completion of reaction, a reaction product is analyzed through gas chromatography. It is confirmed that di-3-methyl-1-butyl carbonate is obtained in a yield of 20%.

Comparative Example 5

Preparation of Carbonic Ester

In a 40 ml autoclave reactor with an external heater, 10 g (29.4 mmol) of tetra-n-butoxy titanium (Ti[O(CH$_2$)$_3$(CH$_3$)]$_4$) is placed, followed by replacing oxygen in the reactor with carbon dioxide. Next, the reactor is heated to 180° C. while stirring, and carbon dioxide is introduced to a pressure of 120 bar, followed by reaction at 180° C. at 120 bar for 1 hour and cooling to room temperature. Thereafter, carbon dioxide is discharged to return the reactor to atmospheric pressure, followed by analyzing a reaction product through gas chromatography. It is confirmed that di-n-butyl carbonate is obtained in a yield of 42%.

Comparative Example 6

Preparation of Carbonic Ester

Reaction is performed in the same manner as in Comparative Example 5 except that reaction pressure (carbon dioxide pressure) is set to 60 bar. After completion of reaction, a reaction product is analyzed through gas chromatography. It is confirmed that di-n-butyl carbonate is obtained in a yield of 30%.

Comparative Example 7

Preparation of Carbonic Ester

In a 40 ml autoclave reactor with an external heater, 10 g (26.4 mmol) of dibutyltin butoxide (Bu$_2$Sn(OBu)$_2$) is placed, followed by replacing oxygen in the reactor with carbon dioxide. Next, the reactor is heated to 180° C. while stirring, and carbon dioxide is introduced to a pressure of 120 bar, followed by reaction at 180° C. at 120 bar for 1 hour and cooling to room temperature. Thereafter, carbon dioxide is discharged to return the reactor to atmospheric pressure, followed by analyzing a reaction product through gas chromatography. It is confirmed that di-n-butyl carbonate is obtained in a yield of 62%.

Comparative Example 8

Preparation of Carbonic Ester

Reaction is performed in the same manner as in Comparative Example 7 except that reaction pressure (carbon dioxide pressure) is set to 60 bar. After completion of reaction, a reaction product is analyzed through gas chromatography. It is confirmed that di-n-butyl carbonate is obtained in a yield of 58%.

The above reaction conditions and yields of carbonic ester are shown in Table 1.

TABLE 1

| | Organometallic compound | | Alcohol | | Reaction temperature (°C.) | Reaction pressure (bar) | Reaction time (h) | Yield (%) |
| --- | --- | --- | --- | --- | --- | --- | --- | --- |
| | Kind | mmol | Kind | mmol | | | | |
| Example 1 | Zr[O(CH$_2$)$_3$CH3]$_4$ | 13 | n-butanol | 326 | 180 | 120 | 1 | 169 |
| Example 2 | Zr[O(CH$_2$)$_3$CH3]$_4$ | 13 | n-butanol | 326 | 180 | 60 | 1 | 110 |
| Example 3 | Ti[O(CH$_2$)$_2$CH(CH$_3$)$_2$]$_4$ | 8 | 3-methyl-1-butanol | 200 | 180 | 280 | 1 | 74 |
| Example 4 | Ti[O(CH$_2$)$_2$CH(CH$_3$)$_2$]$_4$ | 50 | 3-methyl-1-butanol | 100 | 180 | 260 | 1 | 73 |
| Example 5 | Ti[O(CH$_2$)$_3$CH$_3$]$_4$ | 15 | n-butanol | 367 | 180 | 120 | 1 | 98 |
| Example 6 | Ti[O(CH$_2$)$_3$CH$_3$]$_4$ | 15 | n-butanol | 367 | 180 | 60 | 1 | 82 |
| Example 7 | Ti[O(CH$_2$)$_2$CH(CH$_3$)$_2$]$_4$ | 18 | n-propanol | 440 | 180 | 120 | 1 | 70 |
| Example 8 | Ti[O(CH$_2$)$_2$CH(CH$_3$)$_2$]$_4$ | 18 | n-propanol | 440 | 180 | 60 | 1 | 65 |
| Example 9 | Ti[O(CH$_2$)$_3$CH$_3$]$_4$ | 15 | n-butanol | 367 | 180 | 120 | 1 | 97 |
| Comparative Example 1 | Zr[O(CH$_2$)$_3$CH$_3$]$_4$ | 26 | — | — | 180 | 120 | 1 | 67 |
| Comparative Example 2 | Zr[O(CH$_2$)$_3$CH$_3$]$_4$ | 26 | — | — | 180 | 60 | 1 | 55 |
| Comparative Example 3 | Ti[O(CH$_2$)$_2$CH(CH$_3$)$_2$]$_4$ | 50 | — | — | 180 | 230 | 1 | 63 |
| Comparative Example 4 | Ti[O(CH$_2$)$_2$CH(CH$_3$)$_2$]$_4$ | 50 | — | — | 180 | 80 | 1 | 20 |

TABLE 1-continued

| | Organometallic compound | | Alcohol | | Reaction temperature (° C.) | Reaction pressure (bar) | Reaction time (h) | Yield (%) |
|---|---|---|---|---|---|---|---|---|
| | Kind | mmol | Kind | mmol | | | | |
| Comparative Example 5 | Ti[O(CH$_2$)$_3$CH$_3$]$_4$ | 29 | — | — | 180 | 120 | 1 | 42 |
| Comparative Example 6 | Ti[O(CH$_2$)$_3$CH$_3$]$_4$ | 29 | — | — | 180 | 60 | 1 | 30 |
| Comparative Example 7 | Bu$_2$Sn(OBu)$_2$ | 26 | — | — | 180 | 120 | 1 | 62 |
| Comparative Example 8 | Bu$_2$Sn(OBu)$_2$ | 26 | — | — | 180 | 60 | 1 | 58 |

Property Evaluation (1) Evaluation of yield: After completion of reaction, a reaction product is analyzed through gas chromatography.

Yield of carbonic ester (%)=(Mole number of produced carbonic ester/Mole number of added organometallic compound)×100

From the results shown in Table 1, it can be seen that the method according to the present invention uses an organometallic compound, an alcohol, and carbon dioxide at the same time, and thus can prepare a carbonic ester in relatively high yield, as compared with a typical method for preparing a carbonic ester without an alcohol (Comparative Examples 1 to 8). In particular, it can be seen that the method according to the present invention can use a distilled residue after separation of the carbonic ester as the organometallic compound without recycling (Example 9).

Many modifications and other embodiments of the invention will come to mind to one skilled in the art to which this invention pertains. Therefore, it is to be understood that the invention is not to be limited to the specific embodiments disclosed and that such modifications and other embodiments are intended to be included within the scope of the appended claims.

What is claimed is:

1. A method for preparing a carbonic ester, comprising:
reacting carbon dioxide and an alcohol represented by Formula 2:

R$^2$OH     [Formula 2]

wherein R$^2$ is a C$_1$ to C$_8$ alkyl group or a C$_6$ to C$_{10}$ aryl group with an organometallic compound represented by Formula 1:

M(OR$^1$)$_4$     [Formula 1]

wherein M is a Group IV element and each R$^1$ is independently a C$_1$ to C$_8$ alkyl group or a C$_6$ to C$_{10}$ aryl group to prepare a carbonic ester represented by Formula 3:

R$^3$OCOOR$^4$     [Formula 3]

wherein R$^3$ and R$^4$ are the same or different and are each independently a C$_1$ to C$_8$ alkyl group or a C$_6$ to C$_{10}$ aryl group;

recovering the organometallic compound without reacting the organometallic compound to reproduce the organometallic compound; and reacting the recovered organometallic compound with carbon dioxide and an alcohol represented by Formula 2 to prepare additional carbonic ester represented by Formula 3 without reacting the recovered organometallic compound to reproduce the organometallic compound prior to said reacting step.

2. The method according to claim 1, wherein M is titanium (Ti) or zirconium (Zr).

3. The method according to claim 1, wherein R$^1$ is a methyl group, an ethyl group, an n-propyl group, an isopropyl group, an n-butyl group, an isobutyl group, a tert-butyl group, an n-pentyl group, an isopentyl group, an n-hexyl group, or a phenyl group.

4. The method according to claim 1, wherein the reaction is performed at a temperature of about 130° C. to about 230° C. and at a carbon dioxide pressure of about 10 bar to about 300 bar.

5. The method according to claim 1, wherein the first reacting step results in a reaction mixture including the alcohol, the organometallic compound, and the carbonic ester; the recovering step comprising distilling the reaction mixture to provide a mixed distillate of the alcohol and the carbonate ester and a separate distillate of the organometallic compound; and the second reacting step uses the distilled organometallic compound.

* * * * *